Figure 1:
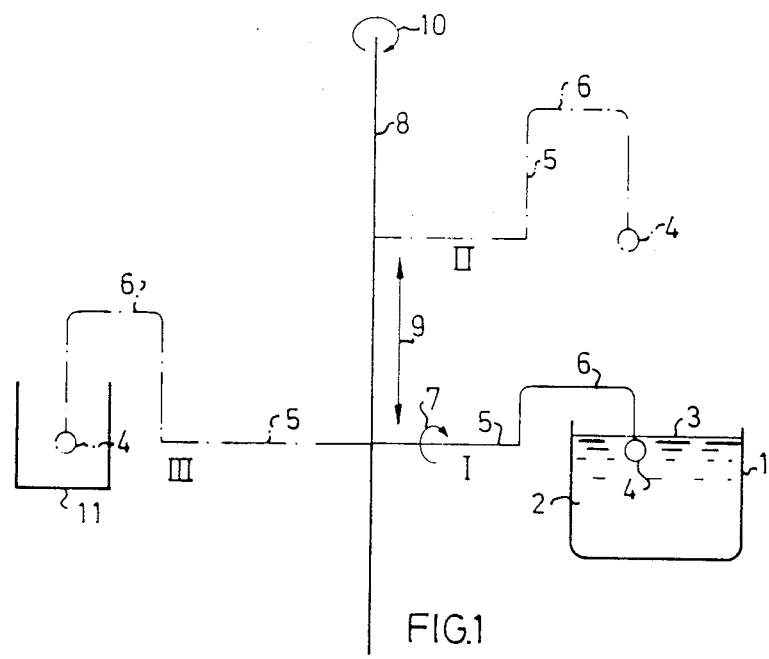

United States Patent [19]

Bäckerud

[11] Patent Number: 4,765,391

[45] Date of Patent: Aug. 23, 1988

[54] ARRANGEMENT FOR USE IN THE THERMAL ANALYSIS AND MODIFICATION OF MOLTEN METAL

[75] Inventor: Stig L. Bäckerud, Lidingö, Sweden

[73] Assignee: Sinter-Cast AB, Viken, Sweden

[21] Appl. No.: 923,829

[22] PCT Filed: Feb. 4, 1986

[86] PCT No.: PCT/SE86/00047

§ 371 Date: Sep. 25, 1986

§ 102(e) Date: Sep. 25, 1986

[87] PCT Pub. No.: WO86/04678

PCT Pub. Date: Aug. 14, 1986

[30] Foreign Application Priority Data

Feb. 5, 1985 [SE] Sweden .................... 8500524

[51] Int. Cl.$^4$ .................... B22D 2/00; B22D 46/00
[52] U.S. Cl. .................... 164/150; 164/4.1; 73/864.63; 73/DIG. 9
[58] Field of Search .................... 164/4.1, 150; 73/864.31, 864.33, 864.51, 864.63, DIG. 9

[56] References Cited

U.S. PATENT DOCUMENTS 4,003,260 1/1977 Catoul .................... 73/864.31
4,204,431 5/1980 Schulz .................... 73/DIG. 9

FOREIGN PATENT DOCUMENTS 350606 10/1972 Sweden .

Primary Examiner—Nicholas P. Godici
Assistant Examiner—Richard K. Seidel
Attorney, Agent, or Firm—Cushman, Darby & Cushman

[57] ABSTRACT

An arrangement for use when thermally analyzing and modifying molten metal, by recording solidification data and controlling the structural modification of the molten metal on the basis of such data. The arrangement includes a sampling container made from a material which remains substantially stable at the temperature of the molten metal and which is adapted to receive at least one thermoelement for recording the solidification data. Means are also provided for taking a sample of the molten metal with the aid of the container, and for moving the sample to an area in which substantially the same conditions prevail. In addition, the arrangement includes recording means and means for modifying the structure of the molten metal as required. The sampling container is constructed to allow molten metal to pass thereinto when the container is immersed into the molten metal, and to allow a previous content of the container to be displaced therefrom and replaced with fresh molten metal as a result of relative movement between the container and the molten metal. Means are provided to ensure that a suitable quantity of molten metal is collected during a sampling operation. This may be achieved by providing the sampling container with openings which are closed and exposed by the valve means or by some other suitable arrangement.

3 Claims, 2 Drawing Sheets

U.S. Patent    Aug. 23, 1988    Sheet 1 of 2    4,765,391

ARRANGEMENT FOR USE IN THE THERMAL ANALYSIS AND MODIFICATION OF MOLTEN METAL

The present invention relates to an apparatus for use when thermally analyzing and modifying molten metal. More specifically, the invention is intended for use when analyzing the solidifying properties of molten metal prior to pouring the metal into moulds, and particularly, although not exclusively, to the solidifying properties of light-metal melts, such as aluminium and magnesium melts.

It is known to analyze thermally the properties of molten metal, hereinafter referred to as melts, and to utilize the results of the analysis to determine the solidification properties of the melt and the post-solidification structure of the metal. It has been found possible to derive from solidification data such properties as the number of nucleants present, the nucleant activity, and the presence of modifying substances with regard to their function during solidification. In this context, a chemical analysis does not provide sufficient information with respect to the ability of the elements present to function as crystallization nuclei and structure modifying additions.

A common method of procedure in this respect is one in which solidification data is determined with the aid of a thermoelement located in the centre of a sample taken from the melt. This sample is of the order of about 100 ml, which is considered sufficiently large to ensure that the thermal capacity of the vessel containing the sample and the thermoelement will not unduly influence solidification. The solidification data assessed is primarily the super-cooling prior to solidification commencing, which reflects the number of primary crystallisation nuclei present and the slope of the temperature curve during the plateau phase as the crystals grow. These values can be recorded digitally and, with the aid of known techniques, compared with desired values of respective magnitudes, and the result obtained therewith utilized in the modification of the solidification properties of the melt, by adding structure modifying substances thereto, or by subjecting the melt to some known metallurgical process effective to change the solidification properties of the melt. In accordance with the invention there is provided an arrangement which can be used to monitor the structure controlling properties of a melt and to control the addition of structure modifying substances thereto, or to control the execution of structure changing measures. The arrangement enables foundries, smelters etc., to be automated to a high extent and also enhances the quality of the goods produced therein.

The arrangement according to the invention for use when thermally analyzing and modifying melts, such as molten metal baths, by recording solidification data of the melt and controlling the possible addition thereto of structure modifying substances on the basis of said analysis is characterized by a sampling container which is made from a material which remains substantially stable at melt temperatures and into which molten metal is able to pass when the container is immersed in the melt; means which are effective to lift the sampling container from the melt, while enclosing a given quantity of molten metal in said container, and to move the container to an area of controlled temperature and to hold the container in said area until the enclosed molten metal has solidified, and then to return the container to an immersed position in the melt; means for measuring and recording solidification data at one or more locations in the enclosed molten metal during the process of its solidification; means for evaluating the solidification data obtained in relation to data derived from melts of known metallurgical structure; and means which are effective to control the supply of additions to the metal melt; and control means for monitoring continuously structure-influencing additions, by intermittent sampling at suitable time intervals.

The sampling container is conveniently provided with an opening through which molten metal can flow, such as to enable the content of the container to be constantly replaced with fresh molten metal when the container is again immersed in the melt. This is achieved either by placing the container in the path of a flowing melt, or by moving the container through a stationary molten bath. The molten content of the container is replaced continually through the turbulence thus created, or the container may be provided with a suitable opening on one side thereof facing the flow of molten metal and a further opening may be provided on the side of the container opposite to one said side, and the container may include means for closing the further opening, so as to collect a suitable quantity of molten metal in the container.

Figure 2:
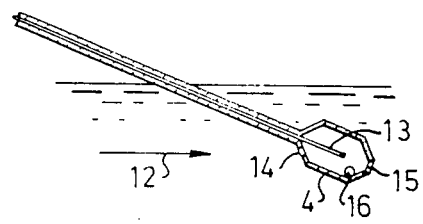
Figure 3:
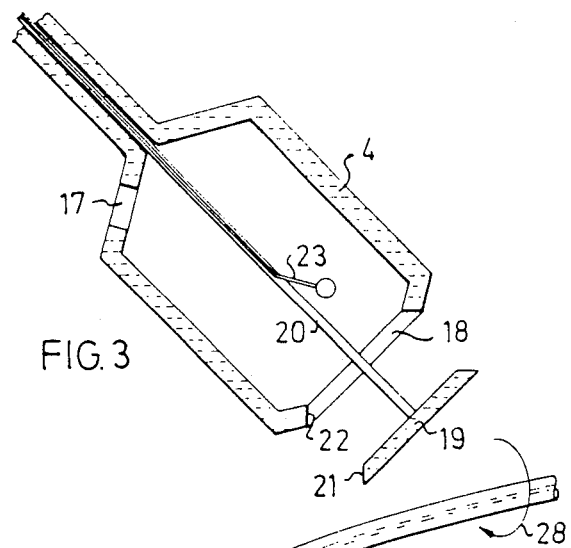
Figure 4:
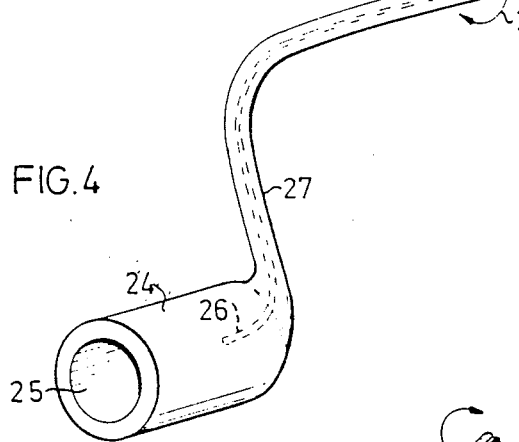
Figure 5:
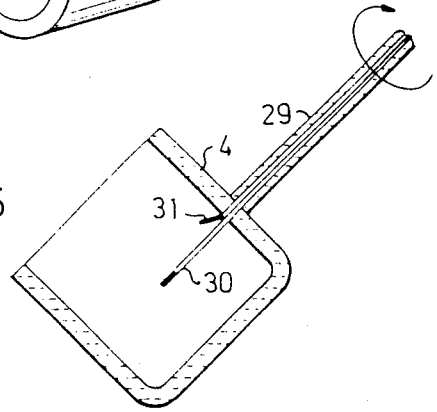

The arrangement according to the invention will now be described in more detail with reference to the accompanying drawings, in which FIG. 1 illustrates schematically an arrangement according to the invention for use in controlling automatically the structure of flowing molten metal;

FIG. 2 illustrates a sampling container lowered in the flow of molten metal; and FIGS. 3–5 illustrate various embodiments of the sampling container.

In FIG. 1 there is shown schematically a chute 1 which conducts flowing molten metal 2 therealong. Immersed beneath the surface 3 of the molten metal 2 is a sampling container 4, which is connected to a horizontal, rotatable shaft 5 through an arcuate part 6. The arrow 7 indicates rotation of the shaft 5. The horizontal shaft 5 is attached to a vertical shaft 8 for movement therealong, as indicated by the arrow 9. The horizontal shaft 5 is mounted on the vertical shaft 8 in a manner to enable it to be swung around said shaft 8, as illustrated by the arrow 10.

As illustrated in the figure, the shaft 5 can be moved to a position I in which the sampling container 4 is immersed in the molten metal, or melt 2, and therewith oriented so that the molten metal can readily flow through the container. When taking a sample of the flowing molten metal, the shaft 5 is rotated so as to move the sampling container to a position in which it will enclose an adapted quantity of the melt, whereafter the shaft 5 is lifted along the shaft 8 to a position II above the melt, and is then swung around the shaft 8 and lowered to a position III. In this latter position, the container 4 is accommodated in a chamber 11, in which the heat given-off as the molten metal sample in the container solidifies is substantially reproducible, from sample to sample.

FIG. 2 illustrates an embodiment of the sampling container 4, and shows the container immersed in the flowing molten metal 2, the direction of flow being indicated by the arrow 12. Arranged centrally in the sampling container is a thermoelement 13. The container is provided with an inlet opening 14 and an outlet opening 15, through which molten metal flows in temperature equilibrium with the melt. The sampling container is constructed in a manner which will ensure that a representative quantity of molten metal is contained therein when the container is lifted from the melt. The sampling container has provided therein a spherical device 16 made from a material which is inert in relation to the molten-metal sample and having a higher density than said metal. When the container is raised to its vertical position, the spherical device 16 moves down in the container and covers and seals the opening 15, thereby preventing molten metal escaping from the container as it is lifted from the flow of molten metal 2. When the sampling container 4 is again lowered into the flow of molten metal 2, subsequent to recording solidification data, the now solid content of the container will melt and the spherical device 16 will fall back to the position illustrated in FIG. 2, thereby enabling the molten metal to flow freely through the openings 14 and 15, while displacing the remelted content of the container.

FIG. 3 illustrates a further embodiment of the sampling container 4, into which molten metal can flow through an opening 17 and leave the container through a slot 18. The slot 18 is arranged to be closed by means of a plate 19, which is mounted on a centrally located post 20 and arranged for movement towards the sampling container in a manner to co-act sealingly with surfaces 21 and 22 so as to prevent molten metal escaping from the container as it is lifted from the flow of molten metal. A thermoelement 23 is arranged in the sampling container.

FIG. 4 illustrates another embodiment of a sampling container which lies within the scope of the invention. In this embodiment, the sampling container, here referenced 24, is open at its one end 25, which in the FIG. 4 illustration is its upper end, and is provided at its other end, i.e. the bottom end, with a thermoelement 26 and a holder arm 27. In use, the container 24 is moved into the flow of molten metal and the content of the container remaining from a preceding sampling process is displaced from said container by the resultant turbulence and replaced with a fresh sample. For the purpose of determining the solidification data of the sample, the holder arm 27 is rotated about its axis as shown at 29, so as to bring the container 24 to a vertical position, with said one end of the container facing upwards. The sampling container 24 is then moved, in this position, to a temperature-defined region for solidification. This embodiment requires a modified form of the operating unit illustrated in FIG. 1.

FIG. 5 illustrates a simple embodiment of the sampling container 4. In this case, the container 4 is attached to a holder arm 29, and two thermoelements 30 and 31 are inserted from one side at the point of attachment to the holder arm, to enable the temperature of the sample to be measured at the centre thereof and at the wall of the container, as the sample solidifies. With this embodiment, the holder arm is immersed into the flow of molten metal at right angles to said flow, and is then turned to a position in which the container is filled with molten metal through the turbulence created. Subsequent to immersing the container and re-melting the solid content thereof, the container may optionally be lifted from the flow of molten metal and emptied, so as to ensure that the container will be filled with truly fresh molten metal for carrying out the next analysis of the subsequent solidification process.

Alternatively, the sampling container, together with the enclosed sample, can be removed from the flow of molten metal and passed to an area in which conditions are substantially the same as those prevailing in the molten metal flow, whereafter thermoelements are immersed into the sample, for example by attaching the thermoelements to a container lid, or into pockets provided in the container herefor. The thermoelements are preferably pre-heated to the temperature of the molten metal.

It will be understood that it lies within the expertise of one skilled in this art, and within the scope of the invention, to make suitable modifications to the aforedescribed and illustrated sampling containers, and to the means for manipulating the containers, and to the manner in which the solidification data are recorded and utilized.

I claim:

1. An arrangement for effecting the thermal analysis and modification of molten metal, by recording solidification data and controlling a subsequent structure modifying process on the basis of the data obtained, characterized by a sampling container which is intended to be immersed in said molten metal and which is made of a material which remains substantially stable at the temperature of said molten metal, said container being constructed to enable molten metal to enter thereinto when said container is in its immersed stae, and said container being provided on one wall thereof with an opening which co-acts with means effective to close the opening prior to lifting the container from the molten metal and to expose said opening when, subsequent to solidification of the sample, the container is re-immersed in the molten metal and the solidified sample in said container has melted; means which are effective to lift the container from the molten metal while enclosing a given quantity thereof, and to move the container to an area in which substantially the same conditions prevail, and to hold the container in said area until the enclosed sample has solidified, and then to return the container to an immersed position in the molten metal; means which are effective to measure and record solidification data at one or more locations in the sample as said sample solidifies; means for evaluating solidification data in relation to known data derived from melts having a known metallurgical structure; means for controlling the supply of additions to the molten metal, or for subjecting the molten metal to a structure modifying process in a controlled manner; and control means for monitoring continuously structure modifying measures by sampling the molten metal intermittently at suitable time intervals.

2. An arrangement according to claim 1, characterized in that the container is arranged for movement between a vertical position and an immersed, inclined position; in that the container is provided with a first opening which can be brought to face the movement direction of the molten metal, and a second opening which can be brought to face in a direction opposite to that faced by the first opening; and in that the container has arranged therein a spherical device which is effective to close the second opening when the container is moved to its vertical position, and to expose said second opening when the container is moved to its immersed, inclined position.

3. An arrangement according to claim 1, characterized in that the sampling container has a sleeve-like configuration having an opening provided in one end wall thereof; valve-means mounted on a centrally arranged post and operative to expose and close said opening when the container is immersed in the molten metal and in substantially temperature equilibrium therewith; in that the sampling container is attached to a holder tube which accommodates the central post together with electrical conductors associated with a thermo-element located in the container; and in that the container is provided in the end wall opposite said one end wall with an opening through which molten metal can enter the container when immersed in the molten metal.

* * * * *